United States Patent
Zhang et al.

(10) Patent No.: US 9,394,251 B2
(45) Date of Patent: Jul. 19, 2016

(54) SILODOSIN INTERMEDIATE AND PREPARATION METHOD THEREFOR

(75) Inventors: Bin Zhang, Zhejiang (CN); Xiaowei Hu, Zhejiang (CN); Pucha Yan, Zhejian (CN); Xianyi Zhang, Zhejian (CN); Hongjun Gao, Zhejian (CN); Yuanqiang Li, Zhejiang (CN); Daqing Che, Zhejiang (CN)

(73) Assignee: Zhejiang Jiuzhou Pharmaceutical Co., Ltd., Taizhou, Zhejiang (CN)

( * ) Notice: Subject to any disclaimer, the term of this patent is extended or adjusted under 35 U.S.C. 154(b) by 0 days.

(21) Appl. No.: 14/365,638

(22) PCT Filed: Jul. 27, 2012

(86) PCT No.: PCT/CN2012/079253
§ 371 (c)(1),
(2), (4) Date: Jan. 15, 2015

(87) PCT Pub. No.: WO2013/097456
PCT Pub. Date: Jul. 4, 2013

(65) Prior Publication Data
US 2015/0148548 A1    May 28, 2015

(30) Foreign Application Priority Data
Dec. 26, 2011 (CN) .......................... 2011 1 0440481

(51) Int. Cl.
C07D 209/08 (2006.01)
C07F 7/00 (2006.01)
C07F 7/02 (2006.01)
C07F 7/18 (2006.01)
C07F 9/6539 (2006.01)

(52) U.S. Cl.
CPC .............. C07D 209/08 (2013.01); C07F 7/00 (2013.01); C07F 7/02 (2013.01); C07F 7/18 (2013.01); C07F 9/65397 (2013.01); Y02P 20/55 (2015.11)

(58) Field of Classification Search
CPC .................................................... C07D 209/08
See application file for complete search history.

(56) References Cited

U.S. PATENT DOCUMENTS

| | | | |
|---|---|---|---|
| 5,192,785 A | 3/1993 | Lo et al. | |
| 5,194,446 A | 3/1993 | Lo et al. | |
| 6,297,270 B1 | 10/2001 | Beller et al. | |

FOREIGN PATENT DOCUMENTS

| | | | |
|---|---|---|---|
| CN | 101993406 A | 3/2011 | |
| CN | 101993407 A | 3/2011 | |
| JP | 2001-199956 A | 7/2001 | |
| JP | 2002-265444 A | 9/2002 | |
| WO | WO2011124704 A1 | 10/2011 | |
| WO | WO2012062229 A1 | 5/2012 | |

OTHER PUBLICATIONS

Beller, M. et al, Synthesis of 2,3-dihydroindoles, indoles, and anilines by transition metal-free amination of aryl chlorides, Journal of Organic Chemistry, 2001, vol. 66, No. 4, pp. 1403-1412.
English abstract; Chinese Application No. CN 101993406.
English abstract; Chinese Application No. CN 101993407.

(Continued)

Primary Examiner — Shawquia Jackson

(57) ABSTRACT

Disclosed are a silodosin intermediate and a preparation method thereof. The silodosin intermediate has the structure shown by the formula (A). X is hydrogen or bromide and $R^1$ is hydrogen. The formyl group may be a group having the structure shown by the formula I. $R^7$ is a protecting group of carboxyl, and $R^2$ is 3-hydroxypropyl or a group having the structure shown by the formula II. W is a protecting group of hydroxyl. A compound of the formula (A) according to the present invention may further be used for preparing a compound having the structure shown by the formula (D). By means of the intermediate and the preparation method therefor provided by the present invention, high-purity optically pure silodosin can be obtained, and the optical purity is above 99%.

18 Claims, No Drawings

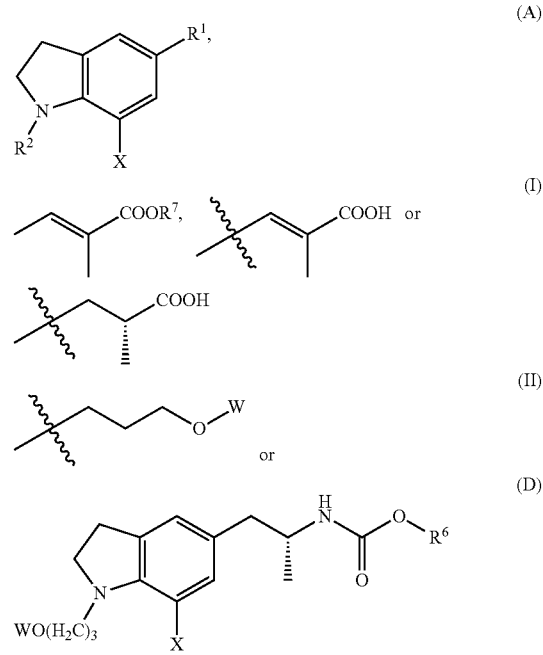

(56) References Cited

OTHER PUBLICATIONS

English abstract; Janpanese Application No. JP2002-265444.
English abstract; Japanese Application No. JP2001-199956.
International Search Report; dated Nov. 1, 2012; International Application No. PCT/CN2012/079253; International Filing Date: Jul. 27, 2012; 4 pages.
English translation; International Search Report; dated Nov. 1, 2012; International Application No. PCT/CN2012/079253; International Filing Date: Jul. 27, 2012; 4 pages.

SILODOSIN INTERMEDIATE AND PREPARATION METHOD THEREFOR

CROSS REFERENCE TO RELATED APPLICATIONS

This application is a national stage application based on PCT/CN2012/079253, filed on Jul. 27, 2012, which claims the priority of China Patent Application No. 201110440481.4, filed with the Patent Office of China on Dec. 26, 2011, titled "SILODOSIN INTERMEDIATE AND PREPARATION METHOD THEREFOR", the contents of which are incorporated herein by reference in its entirety.

FIELD OF THE INVENTION

The present invention relates to the technical field of heterocyclic chemistry, particularly to the technical field of the five-membered nitrogen heterocyclic chemistry.

BACKGROUND OF THE INVENTION

Silodosin is a α1-receptor antagonist developed by Japan, Kissei Pharmaceutical Co., Ltd, and is used clinically to treat dysuria associated with benign prostatic hyperplasia, with chemical name 2,3-dihydro-1-(3-hydroxypropyl)-5[(2R)-2-[2-[2[(2,2,2-trifluoroethoxy)phenyloxy]ethylamino]propyl]-1H-indole-7-carboxamide. the structural formula thereof is shown in the following:

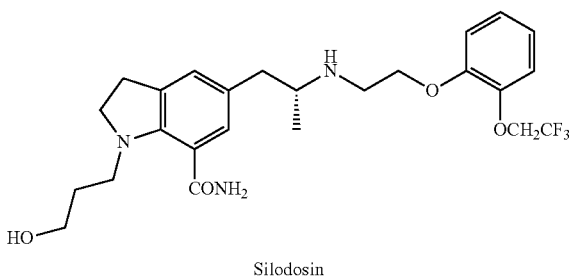

Silodosin

Optically pure silodosin is obtained mainly by performing a chiral resolution of the racemic intermediates produced from different routes in the current literatures. Besides, unsatisfactory reagents are used in some reaction. For example, Europe patent no. EP0600675 disclosed that the racemic intermediate of formula a synthesized by multi-steps from 1-acetylindoline was resolved with tartaric acid to produce the optically pure compound of formula a.

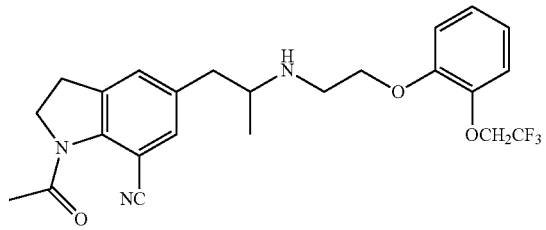

a

The route for preparing silodosin disclosed in Europe patent no. EP0600675 involves multi-steps (12 steps), the use of expensive platinum oxide, toxic sodium cyanide and inflammable and explosive sodium azide which is unfavorable for the labor and environment protection. Thus, it is not available for industrialization.

China patent application with publication no. CN101759627 also disclosed that the racemic intermediate of formula a synthesized by multi-steps from 1-acetylindoline was resolved with tartaric acid, and then subjected to subsequent steps. Reagents in this process included 2-bromo-propionyl chloride, N-bromosuccinimide and trifluoroacetic acid which was used twice, wherein, 2-bromo-propionyl chloride was difficult to obtain, N-bromosuccinimide participating in radical reaction could form more by-products instead of pure monobromination product, and trifluoroacetic acid would cause serious corrosion to equipment. This process is difficult in operation due to these disadvantages and not favorable for commercial production.

Japan patent application with publication no. JP2002265444 disclosed that the racemic intermediate of formula b produced by multi-steps from indoline was separated using (1R,2S)-(–)-benzylaminocyclohexanemethanol as resolving agent to afford the optically pure compound of formula b:

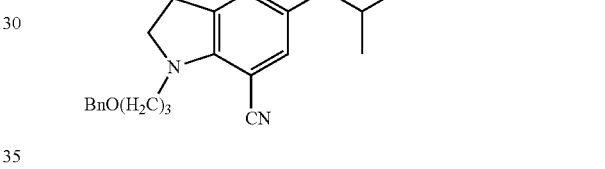

b

Resolving agent is expensive and difficult to recover. In order to get product with higher ee value in these separation methods, recrystallization steps should be repeated many times, which will result in big waste of raw materials, economic loss and environmental pollution. Besides, before optically pure compound of formula b was converted into the compound of formula c, amide must be prepared from the compound of formula b, followed by hoffmann degradation. Thus, the disclosed process gives extra steps and lower yield.

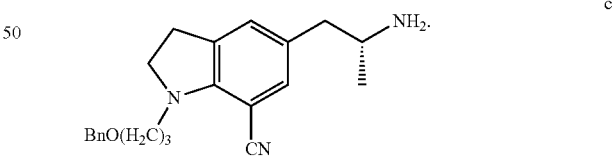

c

SUMMARY OF THE INVENTION

To solve the problems in the disclosed prior art below, such as the use of resolving agent in the reaction process and repeated recrystallization, waste of raw materials, serious product loss, high cost, low yield, heavily polluted reagent with high toxicity and et al, the present invention provides a novel intermediate compound for preparing the optically pure silodosin with the specific proposal as follows:

A compound of formula A having the following structure:

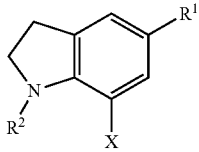

Wherein X is hydrogen or bromine, $R^1$ is hydrogen, formoxyl or a group selected from the following structures:

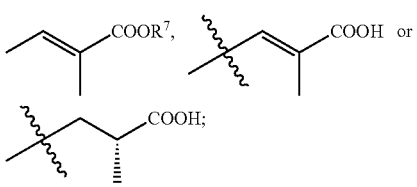

Wherein, $R^7$ is a protecting group of carboxyl.

Preferably, $R^7$ is selected from alkyl and substituted alky, preferably, the alky is aralkyl or substituted aralky.

More preferably, the alkyl is methyl, ethyl or propyl; the substituted alky is trichloromethyl, trifluoromethyl, benzyl, p-methoxybenzyl, p-nitrobenzyl, m-nitrobenzyl, p-chlorobenzyl, m-chlorobenzyl, p-bromobenzyl, m-bromobenzyl, or benzyl.

$R^2$ is 3-hydroxypropyl or a group having the following structure:

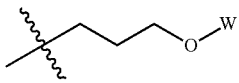

Wherein W is a protecting group of hydroxyl;

Preferably, W is selected from acetyl, trifluoroacetyl, allyloxycarbonyl, tert-butylcarbonyl (Boc), trimethylsilyl (TMS), tert-butyldimethylsilyl (TBDMS), benzoyl, triphenylmethyl, p-methoxybenzyl, p-methoxybenzoxycarbonyl, p-nitrobenzyl, m-nitrobenzyl, p-chlorobenzyl, m-chlorobenzyl, p-bromobenzyl, m-bromobenzyl, and benzyl.

Preferably, the compound of formula A is selected from the compounds having the following structures:

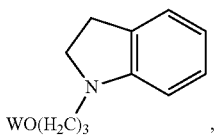

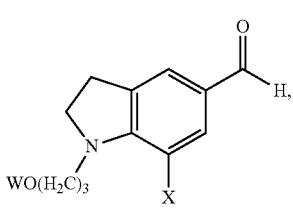

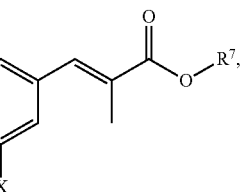

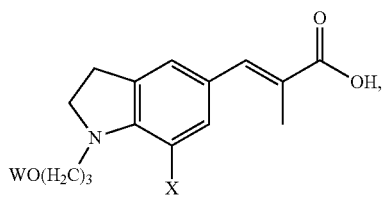

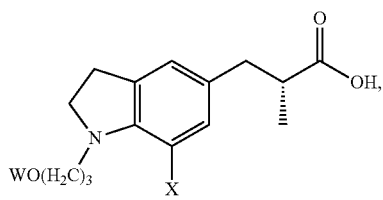

Wherein X, W and $R^7$ are as defined above.

The compound of formula A-2 is obtained by reacting the compound of formula A-1 with the compound of formula C (known as phosphorus glide) having the following structure.

$$Ph_3P=C(CH_3)COOR^7 \qquad C$$

Wherein $R^7$ is as defined above.

The compound of formula C may be prepared according to the procedure described in Tetrahedron, 66(26), 4745-4759; 2010 or J. Org. Chem. 1984, 49, 4293-4295.

Preferably, the molar ratio of the compound of formula A-1 to the compound of formula C is 1 to (1~4).

The preferred solvent for preparing the compound of formula A-2 is selected from amides and aromatic hydrocarbons solvents, and the preferred amides solvent is N,N-dimethylformamide (DMF), N,N-diethylacetamide (DEA), N,N-dimethylpropionamide (DMP) or N,N-diethylpropionamide (DEP); the preferred aromatic hydrocarbons solvent is benzene, methylbenzene or dimethylbenzene. The mass of the solvent is 20-100 times that of the compound of formula A-1, preferably, 30-60 times.

According to the solvent for preparing the compound of formula A-2, those skilled in the art may select the preferred reaction temperature. The preferred reaction temperature is 50° C. to reflux, and the time is 1-20 hours.

The compound of formula A-2 is subjected to hydrolyzation, in the presence of base, to obtain the compound of formula A-3.

The preferred base for preparing the compound of formula A-3 is selected from alkali metal base; the preferred alkali metal base is selected from lithium hydroxide, sodium hydroxide, potassium hydroxide, cesium hydroxide, sodium carbonate, potassium carbonate, sodium bicarbonate or potassium bicarbonate.

The molar ratio of the compound of formula A-2 to the base is 1 to 1-10, preferably, 1 to 2-6.

The preferred solvent for preparing the compound of formula A-3 is selected from polar aprotic solvents. The preferred polar aprotic solvents are alcohols or water, and the alcohols are selected from methanol, ethanol, propanol and n-butanol et al. the mass of the solvent is 10-50 times that of the compound of formula A-2, preferably, 20-30 times.

According to the solvent for preparing the compound of formula A-3, those skilled in the art may select the preferred reaction temperature. The preferred temperature is 0-90° C., and the time is 2-24 hours.

The compound of formula A-3 is subjected to asymmetric catalytic hydrogenation, in the presence of base, to obtain the compound of formula A-4.

The preferred base for preparing the compound of formula A-4 is selected from alkali metal base and organic base. The preferred alkali metal base is selected from lithium hydroxide, sodium hydroxide, potassium hydroxide, cesium hydroxide, sodium bicarbonate, potassium bicarbonate, sodium carbonate, potassium carbonate and cesium carbonate. The preferred organic base is selected from amines. The preferred amines solvent is selected from arylamine and alkylamine. The specific embodiment may be aniline, N,N-dimethylaniline, N-methyl morpholine, diisopropylamine, N,N-isopropylethylamine, triethylamine or pyridine.

The catalyst for preparing the compound of formula A-4 is $Ir(L_1)(L_2)nY$:

Wherein $L_1$ is defined as $(S_a,S)$-SIPHOX:

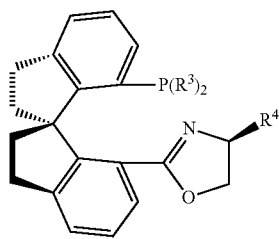

$(S_a,S)$-SIPHOX

Wherein $R^3$ is aryl; preferably, $C_6$~$C_{1-6}$ aryl, $R^4$ is hydrogen, alkyl, aryl or aralkyl; the preferred alkyl is selected from $C_1$~$C_8$ alkyl; the preferred aryl is selected from $C_6$~$C_{16}$ aryl; the preferred aralkyl is selected from $C_7$~$C_{16}$ aralkyl.

The preferred $L_2$ is selected from cyclooctene, 1,5-cyclooctadiene, ethylene, 1,5-hexadiene or norbornadiene.

n is 1 or 2.

Y is chloride ion, bromide ion, iodide ion, fluoride ion, trifluoroacetate ion, tetrafluoro borate radical, tetra(3,5-bis(trifluoromethyl)phenyl)borate radical, tetraphenyl borate radical, hexafluoro antimonite radical, hexafluoro phosphate ion, trifluoro methanesulfonate ion, methanesulfonate ion, perchlorate ion, perbromate ion, periodate ion, nitrate radical, bisulphate radical, acetylacetonate ion.

Preferably, the molar ratio of the compound of formula A-3 to the base is 1 to 1~3.

The molar ratio of the compound of formula A-3 to $Ir(L_1)(L_2)nY$ is 1 to 0.00001-0.04, preferably, 1 to 0.0001-0.005.

The hydrogen pressure for preparing the compound of formula A-4 is 0.1-10 Mpa, preferably, 0.5-1.0 Mpa.

The preferred solvent for preparing the compound of formula A-4 is selected from alcohols, ethers or mixtures thereof. The preferred alcohols are selected from methanol, ethanol, isopropanol, n-propanol, n-butanol or a mixture of any two or more thereof. The preferred ethers are selected from tetrahydrofuran and methyltetrahydrofuran. The mass of the solvent is 20-80 times that of the compound of formula A-3, preferably, 30-80 times.

According to the solvent for preparing the compound of formula, those skilled in the art may select the preferred reaction temperature. The preferred temperature is 30-70° C., and the preferred reaction time was 0.5-10 hours.

The compound of formula A-4, in the presence of diphenylphosphoryl azide and diisopropylethylamine, by further reacting with the compound of formula E having the following structure, is converted into the compound of formula D having following structure

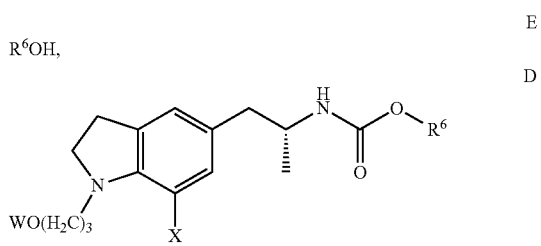

Wherein X, W is as defined above, $R^6$ is a protecting group of carboxyl, and the specific embodiment is tert-butyl, ethenyl, allyl, benzyl, p-methoxybenzyl, p-nitrobenzyl or diphenylmethyl.

The compound of formula D is converted further to Silodosin. The reaction may be performed according to the method described in Japan publication no. JP2006188470.

When X is bromine, the compound of formula A is obtained by reacting the compound of formula B with bromine.

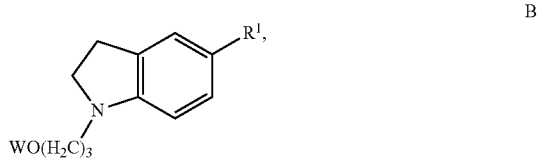

Wherein, $R^1$ and W are as defined above.

Preferably, the molar ratio of the compound of formula B to the bromine is 1 to 1-2.

The preferred solvent for preparing the compound of formula A is selected from chloroalkane and amines. The preferred chloroalkane is selected from dichloromethane, chloroform; the preferred amine is selected from N,N-dimethyl formamide and N,N-diethylacetamide.

The mass of the solvent for preparing the compound of formula A is 15-60 times that of the compound of formula B, preferably, 20-40 times.

The preferred temperature for preparing the compound of formula A is −10-10° C.

The compound of formula A is used for preparing silodosin.

In a preferred technical proposal, the compound of formula A is selected from the compounds having the following structures:

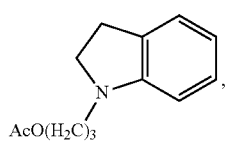

-continued

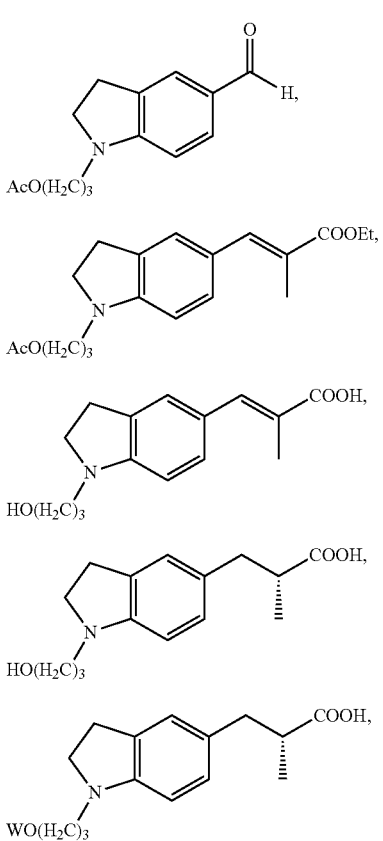

Wherein W is as defined above.

The compound of formula 1 is obtained by reacting indoline with 3-chloropropyl acetate by electrophilic substitution in the presence of a base.

The preferred base for preparing the compound of formula 1 is selected from amines. The preferred amines are arylamine or alkylamine, and the specific embodiment is aniline, N,N-dimethylaniline, N-methyl morpholine, diisopropylamine, N,N-isopropylethylamine, triethylamine or pyridine.

The molar ratio of indoline to 3-chloropropyl acetate is 1 to 1-3.

The molar ratio of indoline to the base is 1 to 1-3.

The preferred solvent for preparing the compound of formula 1 is selected from polar aprotic solvents. The preferred polar aprotic solvents are alcohols, and the alcohols are methanol, ethanol, propanol or n-butanol. The mass of the solvent is 20-100 times that of indoline, preferably, 40-60 times.

The reaction temperature for preparing the compound of formula 1 is 60° C. to reflux, and the reaction time is 6-24 hours.

The compound of formula 2 is obtained by reacting the compound of formula 1 with $POCl_3$.

The molar ratio of the compound of formula 2 to $POCl_3$ was 1 to 1-3.

The preferred solvent for preparing the compound of formula 2 is amides, the preferred amides is N,N-dimethylformamide or N,N-diethylacetamide. The mass of the solvent is 20-100 times that of the compound of formula 1, preferably, 40-60 times.

The reaction temperature for preparing the compound of formula 2 is −10° C. to 40° C., and the reaction time is 2-20 hours.

The compound of formula 3 is obtained by reacting the compound of formula 2 (known as phosphorus glide) with the compound of formula b having the following structure.

$Ph_3P=C(CH_3)CO_2Et$  b

The compound of formula b may be prepared according the procedure described in Tetrahedron, 66(26), 4745-4759; 2010.

The molar ratio of the compound of formula 2 to the compound of formula b is 1 to 1-4.

The preferred solvent for preparing the compound of formula 3 is amides, the preferred amides is N,N-dimethylformamide or N,N-diethylacetamide. The mass of the solvent is 20-100 times that of the compound of formula 2, preferably, 30-60 times.

The preferred reaction temperature for preparing the compound of formula 3 is 50° C. to reflux, and the reaction time is 1-20 hours.

The compound of formula 4 is obtained by reacting the compound of formula 3 with a base.

The preferred base is alkali metal base. The preferred alkali metal base is selected from lithium hydroxide, sodium hydroxide, potassium hydroxide, cesium hydroxide.

The molar ratio of the compound of formula 3 to the base is 1 to 1-10, preferably, 1 to 2-6.

The preferred solvent for preparing the compound of formula 4 is selected from polar aprotic solvents. The preferred polar aprotic solvents are alcohols or water, and the alcohols are selected from methanol, ethanol, propanol and n-butanol et al. the mass of the solvent is 10-50 times that of the compound of formula 3, preferably, 20-30 times.

The preferred reaction temperature for preparing the compound of formula 4 is 0-40° C., and the reaction temperature is 2-24 hours.

The compound of formula 4 is subjected to catalytic hydrogenation, in the presence of base, to obtain the compound of formula 5.

The preferred base is selected from alkali metal base and organic base. The preferred alkali metal base is selected from lithium hydroxide, sodium hydroxide, potassium hydroxide, cesium hydroxide, sodium bicarbonate, potassium bicarbonate, sodium carbonate, potassium carbonate and cesium carbonate. The preferred organic base is selected from amines. The preferred amines are selected from arylamine and alkylamine. The specific embodiment may be aniline, N,N-dimethylaniline, N-methyl morpholine, diisopropylamine, N,N-isopropylethylamine, triethylamine or pyridine.

The catalyst for preparing the compound of formula 5 is $Ir(L_1)(L_2)nY$:

Wherein $L_1$ is defined as (Sa,S)-SIPHOX:

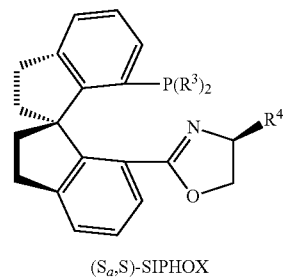

$(S_a,S)$-SIPHOX

Wherein $R^3$ is aryl; preferably, $C_6\sim C_{1-6}$ aryl, $R^4$ is hydrogen, alkyl, aryl or aralkyl; the preferred alkyl is selected from $C_1$~$C_8$ alkyl; the preferred aryl is selected from $C_6$~$C_{1-6}$ aryl; the preferred aralkyl is selected from $C_7$~$C_{16}$ aralkyl.

The preferred $L_2$ is selected from cyclooctene, 1,5-cyclooctadiene, ethylene, 1,5-hexadiene or norbornadiene.

n is 1 or 2.

Y is chloride ion, bromide ion, iodide ion, fluoride ion, trifluoroacetate ion, tetrafluoro borate radical, tetra(3,5-bis (trifluoromethyl)phenyl)borate radical, tetraphenyl borate radical, hexafluoro antimonite radical, hexafluoro phosphate ion, trifluoro methanesulfonate ion, methanesulfonate ion, perchlorate ion, perbromate ion, periodate ion, nitrate radical, bisulphate radical, acetylacetonate ion.

Preferably, the molar ratio of the compound of formula 4 to the base is 1 to 1~3.

The molar ratio of the compound of formula 4 to $Ir(L_1)(L_2)$ nY is 1 to 0.00001-0.04, preferably, 1 to 0.0001-0.005.

The hydrogen pressure for preparing the compound of formula 5 is 0.1-10 Mpa, preferably, 0.5-1.0 Mpa.

The preferred solvent for preparing the compound of formula A-4 is selected from alcohols, ethers or mixtures thereof. The preferred alcohols are selected from methanol, ethanol, isopropanol, n-propanol, n-butanol or a mixture of any two or more thereof. The preferred ethers are selected from tetrahydrofuran and methyltetrahydrofuran. The mass of the solvent is 20-80 times that of the compound of formula 4, preferably, 30-50 times.

The preferred reaction temperature for preparing the compound of formula 5 is 30-70° C., and the reaction temperature is 0.5-10 hours.

The compound of formula 6 is obtained by subjected the compound of formula 5 and electrophilic reagent to electrophilic substitution. And a base may also be added to the reaction system.

Preferably, the electrophilic reagent is selected from acetic anhydride, acetyl chloride, benzyl chloride, benzyl bromide, p-methoxybenzyl bromide.

The preferred base is amines, the preferred amines are selected from arylamine and alkylamine. The specific embodiment may be aniline, N,N-dimethylaniline, N-methyl morpholine, diisopropylamine, N,N-isopropylethylamine, triethylamine or pyridine.

The molar ratio of the compound of formula 5 to the electrophilic reagent is 1 to 1-2.

The molar ratio of the compound of formula 5 to the base is 1 to 1-3.

The preferred solvent for preparing the compound of formula 6 is selected from ethers, alcohols or chloroalkane. The specific embodiment for ethers may be tetrahydrofuran or methyl tert-butyl ether, for alcohols may be methanol, ethanol, isopropanol, n-propanol, n-butanol, isoamylol or a mixture of any two or more thereof, and for chloroalkane may be dichloromethane, chloroform, 1,1-dichloroethane or a mixture of any two or more thereof.

The preferred reaction temperature for preparing the compound of formula 6 is 30° C. to reflux, and the reaction temperature is 5-30 hours.

The advantages of the intermediate and the preparation method thereof provided by the present invention include enriching pharmaceutical intermediates in the field of pharmaceutical and chemical industry, and transformation between them easily through simple types of reaction, such as electrophilic substitution, catalytic hydrogenation and et al, using $Ir(L_1)(L_2)nY$ with high selectivity as catalyst instead of expensive resolving reagent in the process for preparing chiral compound (with the catalyst used, high purity and single enantiomer of intermediate can be obtained, the ee value is over 99% analyzed through chiral HPLC analysis, the said optically purity also can be reached when the molar ratio of the catalyst to substrate is 1 to 10000), low cost, higher yield, raw material saving, avoiding using undesirable reagent, such as 2-bromo-propionyl chloride, N-bromosuccinimide, trifluoroacetic acid, sodium cyanide, sodium azide, high atomic economy and being favorable for environment protection. Hence, the present invention has great value for medical application.

DETAILED EMBODIMENTS

The present invention discloses silodosin intermediate and preparation method therefor. People skilled in the art can refer to the content in the invention and make reasonable adjustment to the technological parameters. It should be particularly noted that all of the similar replacement and modification which is obvious to one skilled in the art are treated as inclusion of the present invention. Since the method and application in the present invention has been described by particular examples with considerable results, relevant technicists are obviously incapable of adjusting and modifying the methods and application described in this article without referring to the content, spirits and scope of the present invention when attempting to realize and apply this technique.

The particular examples below can be helpful to comprehend the present invention. However, the protecting scope of the theme above should not be limited into the following examples. Instead, all the technique achieved based on this invention belong to the present invention.

Example 1

The Preparation of the Compound of formula A-1-1 (W is Acetyl, X is Bromine)

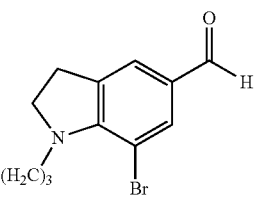

A-1-1

1-(3-(acetyl)propyl)indole-5-formaldehyde (2.0 g, 8.10 mmol) and dichloromethane 40 ml were charged successively into a 100 ml two-neck round-bottom flask. The mixture was cooled to −10-10° C. Bromine (1.36 g, 8.51 mmol) was added drop wise at this temperature. After addition was complete, the reaction mixture was stirred at −10~10° C. The reaction was monitored by TLC until all start raw materials were consumed. After the reaction was complete, saturated aqueous solution of 5 ml sodium sulfite and 10 ml sodium bicarbonate were added with stirring for further 10 minutes. The layers were separated and the organic layer was washed with saturated aqueous solution of 15 ml brine and concentrated to afford 2.57 g the compound of formula A-1-1, with a molar yield of 97.3%.

The compounds in example 2 to 12 were prepared according to the procedure described in example 1, wherein W was selected from various hydroxyl-protecting groups, X is bromine, and the results were summarized in following table:

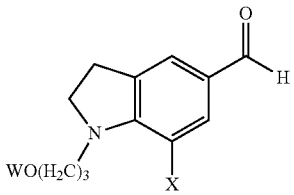

A-1

| Example | Product | W | Yield (%) | m/z |
|---|---|---|---|---|
| 2 | A-1-2 | trifluoroacetyl | 87.0 | 379/380/381 |
| 3 | A-1-3 | allyloxycarbonyl | 92.9 | 367/368/369 |
| 4 | A-1-4 | t-butyloxycarbonyl | 97.7 | 383/384/385 |
| 5 | A-1-5 | trimethylsilyl | 97.1 | 355/357/358 |
| 6 | A-1-6 | tert-butyldimethylsilyl | 96.1 | 397/398/399 |
| 7 | A-1-7 | benzoyl | 86.8 | 387/388/389 |
| 8 | A-1-8 | p-methoxybenzyl | 97.2 | 403/404/405 |
| 9 | A-1-9 | p-methoxybenzyloxycarbonyl | 91.5 | 433/434/435 |
| 10 | A-1-10 | p-nitrobenzyl | 90.1 | 418/419/420 |
| 11 | A-1-11 | p-chlorobenzyl | 92.4 | 407/409/411 |
| 12 | A-1-12 | benzyl | 96.8 | 373/374/375 |

Example 13

The Preparation of the Compound of formula of A-2-1 (W is Acetyl, X is Bromine, $R^7$ is Methyl)

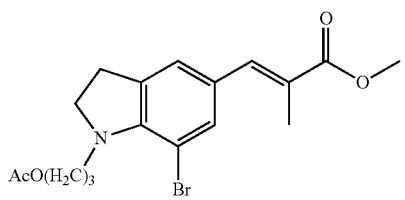

A-2-1

Compound A-1-1 (2.0 g, 6.14 mmol), phosphonium ylide (3.21 g, 9.21 mmol) and methylbenzene 40 ml were charged successively into a 100 ml one-neck round-bottom flask. The mixture was heated to 90~100° C. under nitrogen and maintained at this temperature. The reaction was monitored by TLC until all start raw materials were consumed. After the reaction was complete, the reaction mixture was concentrated under reduced pressure to give a residue which was then purified by column chromatography to afford 1.96 g the compound of formula A-2-1, with a molar yield of 80.7%.

The compounds in example 14 to 24 were prepared according to the procedure described in example 13, wherein W was selected from various hydroxyl-protecting groups, X is bromine, $R^7$ was selected from various carboxyl-protecting groups, and the results were summarized in following table:

A-2

| Example | Product | W | $R^7$ | Yield (%) | m/z |
|---|---|---|---|---|---|
| 14 | A-2-2 | trifluoroacetyl | methyl | 76.1% | 449/450/451 |
| 15 | A-2-3 | allyloxycarbonyl | methyl | 72.0% | 437/438/439 |
| 16 | A-2-4 | t-butyloxycarbonyl | trifluoromethyl | 65.1% | 507/508/509 |
| 17 | A-2-5 | trimetylsilyl | benzyl | 78.7% | 501/503/504 |
| 18 | A-2-6 | t-butyldimethylsilyl | p-methoxybenzyl | 83.5% | 573/575/576 |
| 19 | A-2-7 | benzoyl | p-nitrobenzyl | 68.2% | 578/579/580 |
| 20 | A-2-8 | p-methoxybenzyl | p-chlorobenzyl | 70.9% | 583/585/586 |
| 21 | A-2-9 | p-methoxybenzylcarbonyl | benzyl | 83.3% | 593/594/595 |
| 22 | A-2-10 | p-nitrobenzyl | propyl | 85.3% | 516/517/518 |
| 23 | A-2-11 | p-chlorobenzyl | ethyl | 80.0% | 491/493/494 |
| 24 | A-2-12 | benzyl | ethyl | 78.9% | 457/458/459 |

Example 25

The Preparation of the Compound of formula A-3-1 (W is Benzyl, X is Bromine)

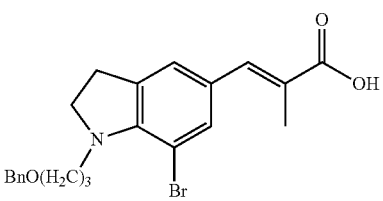

A-3-1

Compound of formula A-2-12 (2 g, 4.37 mmol), 50% aqueous solution of potassium hydroxide (0.73 g, 6.48 mmol) and methanol 30 ml were charged into a 100 ml one-neck round-bottom flask. The mixture was heated to reflux. The reaction was monitored by TLC until all start raw materials were consumed. After the reaction was complete, the reaction mixture was concentrated to dryness to give a residue which was then purified by column chromatography to afford 1.84 g the compound of formula A-3-1, with a molar yield of 97.9%.

$^1$H NMR (400 MHz, DMSO): δ=1.80-1.87 (m, 2H), δ=2.02 (s, 3H), δ=2.96 (t, J=8.8 Hz, 2H), δ=3.49-3.54 (m, 4H), δ=3.61 (t, J=7.6 Hz, 2H), δ=4.47 (s, 2H), δ=7.19 (s, 1H), δ=7.27-7.37 (m, 6H), δ=7.41 (s, 1H), δ=12.26 (s, 1H).

The example 25 was repeated by subject the products obtained in example 20 to 24 as starting materials to hydrolyzation, to obtain the compounds in examples 26 to 29, and the results were summarized in the following table:

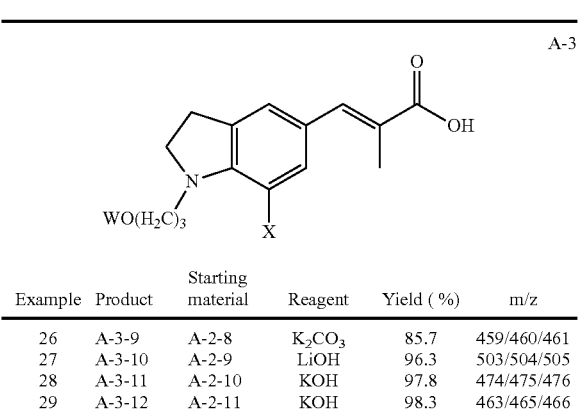

A-3

| Example | Product | Starting material | Reagent | Yield (%) | m/z |
|---|---|---|---|---|---|
| 26 | A-3-9 | A-2-8 | $K_2CO_3$ | 85.7 | 459/460/461 |
| 27 | A-3-10 | A-2-9 | LiOH | 96.3 | 503/504/505 |
| 28 | A-3-11 | A-2-10 | KOH | 97.8 | 474/475/476 |
| 29 | A-3-12 | A-2-11 | KOH | 98.3 | 463/465/466 |

Example 30

The Preparation of the Compound of formula A-4-1
(W is Benzyl, X is Bromine)

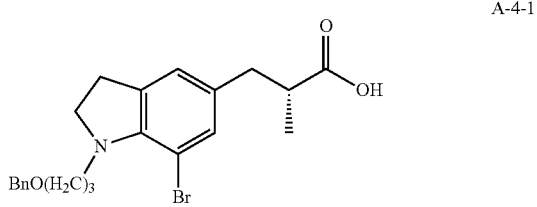

A-4-1

The compound of formula A-3-1 (2 g, 4.65 mmol) and catalyst $Ir(L_1)(L_2)_nY$ (0.74 g, 0.00078 mmol) (the catalyst with $R^3$ being phenyl, $R^4$ being benzyl, $L_2$ being Cyclooctene, n being 1 and Y being tetrafluoro borate radical) (the catalyst was supplied by Zhejiang Jiuzhou Pharmaceutical Co., Ltd) were weighed in the reaction inner tube with a stirring bar. Triethylamine (0.47 g, 4.7 mmol) and 150 ml anhydrous methanol was added. After increasing the hydrogen pressure up to 12 Mpa, the reaction mixture was stirred under hydrogen gas at 70° C. till the pressure stopped declining. Then the stirring was stopped, the hydrogen was released. After the reaction system was concentrated, the system was diluted with 100 ml ether and was adjusted with 3N hydrochloric acid water solution to acidity. The layers were separated, and the aqueous layer was extracted with ether for two times. The combined organic layers were washed with brine and dried over anhydrous sodium sulfate, and concentrated to afford 1.91 g the crude compound of formula A-4-1. The conversion rate is over 99% analyzed through $^1$HNMR, the ee value is over 99% analyzed through chiral HPLC analysis. The crude compound of formula A-4-1 was purified by column chromatography to afford the product, with a yield of 95.0%.

$^1$H NMR (400 MHz, $CDCl_3$): $\delta$=1.15 (d, J=6.8 Hz, 3H), $\delta$=1.87-1.94 (m, 2H), $\delta$=2.46-2.52 (m, 1H), $\delta$=2.61-2.70 (m, 1H), $\delta$=2.89-2.95 (m, 3H), $\delta$=3.45 (t, J=8.4 Hz, 2H), $\delta$=3.57-3.60 (m, 4H), $\delta$=4.52 (s, 2H), $\delta$=6.80 (s, 1H), $\delta$=7.00 (s, 1H), $\delta$=7.25-7.34 (m, 5H), $\delta$=9.52 (s, 1H).

The compounds in examples 31~48 were prepared according to the procedure described in example 30, wherein, W is benzyl or p-methoxybenzyl, X is bromine, catalyst $Ir(L_1)(L_2)_nY$ carries various substituent groups. The results were summarized in the following table:

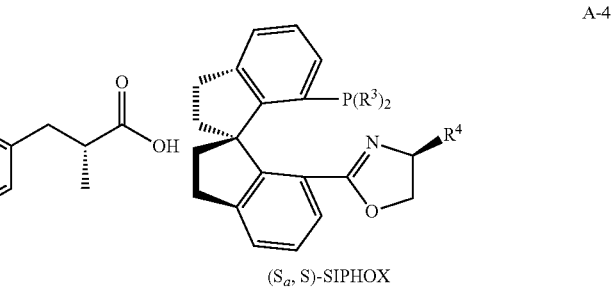

A-4

($S_a$, S)-SIPHOX

| Example | W | $R^3$ | $R^4$ | $L_2$ | n | Y | ee (%) | Yield (%) |
|---|---|---|---|---|---|---|---|---|
| 31 | benzyl | phenyl | hydrogen | cyclooctyl | 1 | chloride ion | >99 | 90 |
| 32 | benzyl | phenyl | ethyl | cyclooctyl | 1 | trifluoroacetate ion | | 91 |
| 33 | benzyl | 2,5-diisopropylphenyl | benzyl | 1,5-cyclooctadiene | 1 | tetra(3,5-bis(trifluoromethyl)phenyl)borate radical | >99 | 95 |
| 34 | benzyl | 2,5-diisopropylphenyl | phenyl | 1,5-cyclooctadiene | 1 | tetraphenyl borate radical | >99 | 97 |
| 35 | benzyl | p-methylphenyl | ethyl | ethylene | 1 | hexafluoro phosphate ion | >99 | 97 |
| 36 | benzyl | 2-isobutyl-pheyl | benzyl | 1,5-hexadiene | 2 | trifluoro methanesulfonate ion | >99 | 93 |
| 37 | benzyl | 2-methylphenyl | p-methylphenyl | 1,5-hexadiene | 2 | perchlorate | >99 | 98 |
| 38 | benzyl | 3,5-diisopentylphenyl | 3,5-diisopentylphenyl | norbornadiene | 2 | nitrate radical | >99 | 95 |
| 39 | benzyl | 3-isopropylphenyl | 4-methylbenzy | norbornadiene | 2 | bisulphate radical | >99 | 94 |

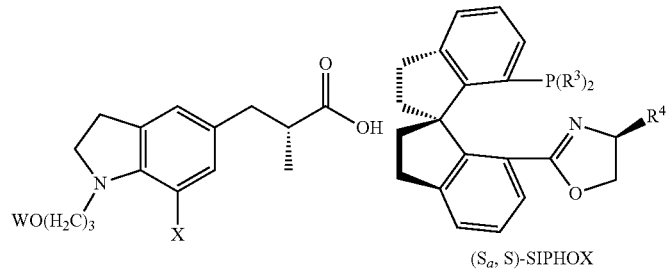

(S$_a$, S)-SIPHOX

A-4

| Example | W | R³ | R⁴ | L₂ | n | Y | ee (%) | Yield (%) |
|---|---|---|---|---|---|---|---|---|
| 40 | p-methoxybenzyl | phenyl | hydrogen | Cyclooctene | 1 | chloride ion | >99 | 91 |
| 41 | p-methoxybenzyl | phenyl | ethyl | Cyclooctene | 1 | trifluoroacetyl | >99 | 91 |
| 42 | p-methoxybenzyl | 2,5-diisopropylphenyl | benzyl | 1,5-cyclooctadiene | 1 | tetra(3,5-bis(trifluoromethyl)phenyl)borate radical | >99 | 96 |
| 43 | p-methoxybenzyl | 2,5-diisopropylphenyl | phenyl | 1,5-cyclooctadiene | 1 | tetraphenyl borate radical | >99 | 97 |
| 44 | p-methoxybenzyl | p-methylphenyl | ethyl | ethylene | 1 | hexafluoro phosphate ion | >99 | 96 |
| 45 | p-methoxybenzyl | 2-isobutylphenyl | benzyl | 1,5-hexadiene | 2 | trifluoro methanesulfonate ion | >99 | 95 |
| 46 | p-methoxybenzyl | p-methylphenyl | p-methylphenyl | 1,5-hexadiene | 2 | perchlorate ion | >99 | 99 |
| 47 | p-methoxybenzyl | 3,5-diisopentylphenyl | 3,5-diisopentylphenyl | norbornadiene | 2 | nitrate radical | >99 | 98 |
| 48 | p-methoxybenzyl | 3-isopropylphenyl | 4-methylbenzyl | norbornadiene | 2 | bisulphate radical | >99 | 93 |

Example 49

The Preparation of the Compound of formula D-1 (W is Benzyl, X is Bromine, R⁶ is Benzyl)

D-1

The compound of formula (25.0 g, 57.8 mmol), diphenylphosphoryl azide (15.9 g, 57.8 mmol) and diisopropylethylamine were charged successively into 500 ml one-neck round bottom flask and then heated to 60~65° C. and maintained at this temperature for 1 to 3 hours. benzyl alcohol (9.4 g, 87.0 mmol) was added, heated to 90~95° C. and maintained at this temperature for 10 to 24 hours. After the completion of the reaction, the reaction mixture was concentrated under reduced pressure. The residue was purified by column chromatography to afford 24.1 g the compound of formula D-1, with a molar yield of 77.7%.

$^1$H NMR (400 MHz, CDCl$_3$): δ=1.09 (d, J=6.8 Hz, 3H), δ=1.87-1.94 (m, 2H), δ=2.47-2.52 (m, 1H), δ=2.66-2.71 (m, 1H), δ=2.92 (t, J=8.8 Hz, 2H), δ=3.45 (t, J=8.8 Hz, 2H), δ=3.57-3.60 (m, 4H), δ=3.83-3.91 (m, 1H), δ=4.52 (s, 2H), δ=4.59-4.63 (m, 1H), δ=5.09 (s, 2H), δ=6.79 (s, 1H), δ=6.97 (s, 1H), δ=7.25-7.37 (m, 10H).

The example 49 was repeated by using the products as starting materials selected from example 31 to 48, to obtain the compounds in examples 50 to 57, and the results were summarized in the following table:

D

| Example | W | R⁶ | Reagent | Yield (%) | m/z |
|---|---|---|---|---|---|
| 50 | benzyl | tert-butyl | tert-butyl alcohol | 72.1 | 502/503/504 |
| 51 | benzyl | p-methoxybenzyl | p-methoxybenzyl alcohol | 65.0 | 566/567/568 |
| 52 | benzyl | p-nitrobenzyl | p-nitrobenzyl alcohol | 55.4 | 581/582/583 |
| 53 | benzyl | diphenylmethyl | diphenylmethanol | 57.2 | 612/613/614 |
| 54 | p-methoxybenzyl | tert-butyl | tert-butyl alcohol | 71.5 | 532/533/534 |
| 55 | p-methoxybenzyl | p-methoxybenzyl | p-methoxybenzyl alcohol | 62.3 | 596/597/598 |
| 56 | p-methoxybenzyl | p-nitrobenzyl | p-nitrobenzyl alcohol | 50.2 | 611/612/613 |

-continued

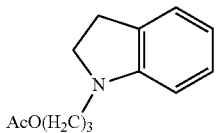

| Example | W | R⁶ | Reagent | Yield (%) | m/z |
|---|---|---|---|---|---|
| 57 | p-methoxy-benzyl | diphenyl-methyl | diphenyl methanol | 52.9 | 642/643/645 |

Example 58

The Preparation of Formula 1

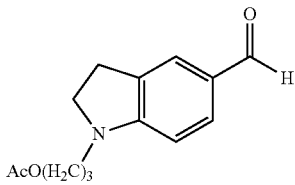

Indoline (92.05 g, 0.774 mol), 3-chloropropanolacetate (122.0 g, 0.893 mol) and N,N-diisopropyl ethylamine (336.2 mL, 1.935 mol) were charged successively into 1000 ml tree-neck round-bottom flask, equipped with a mechanical stirrer and reflux condenser. Isopropanol was added and then reacted at reflux for 12 hours. Most of the isopropanol in the reaction liquid was removed by distillation under reduced pressure. The mixture was extracted with ethyl acetate. The organic layer was dried over anhydrous sodium sulfate. Removal of the solvent by distillation under reduced pressure afforded 189 g the crude compound of formula 1 as a deep red solid, which was used directly in the next step without further purification.

$^1$HNMR (400 MHz, CDCl$_3$): δ=1.953-1.987 (m, 2H), δ=2.102 (s, 3H), δ=2.971-3.012 (t, 2H, J=8.4 Hz), δ=3.159-3.195 (t, 2H, J=7.2 Hz), δ=3.346-3.388 (t, 2H, J=8.4 Hz), δ=4.203-4.235 (t, 2H, J=6.4 Hz), δ=6.484-6.504 (d, 1H, J=8 Hz), δ=6.660-6.697 (t, 1H, J=7.2 Hz), δ=7.072-7.110 (m, 2H).

Example 59

The Preparation of the Compound of formula 2

400 ml N,N-dimethylformamide was charged into a tree-neck flask equipped with a thermometer and mechanical stirrer, and then POCl$_3$ (163 g, 1.07 mol) was added drop wise in an ice-water bath over 20~30 minutes, and maintained in this bath with stirring for 30 minutes. A solution of the compound of formula 1 (156 g, 0.713 mol) in N,N-dimethylformamide was added drop wise over 20~30 minutes and then heated to 30° C. with reacting for 2~5 hours. The reaction was monitored by TLC until the completion of the reaction. The resulting mixture was poured into cold water and the impurities among it were extracted with 200 ml ethyl acetate. The aqueous layer was adjusted to pH>13 with 50% NaOH solution and stirred evenly, extracted with 800 ml ethyl acetate. The organic layer was dried over anhydrous MgSO$_4$. Removal of the solvent under reduced pressure afforded 150.2 g the compound of formula 2 as a white solid, with a yield of 85.3%.

$^1$HNMR (400 MHz, CDCl$_3$): δ=1.927-1.993 (m, 2H), δ=2.074 (s, 3H), δ=3.041-3.083 (t, 2H, J=8.4 Hz), δ=3.301-3.337 (t, 2H, J=7.2 Hz), δ=3.580-3.623 (t, 2H, J=8.4 Hz), δ=4.140-4.171 (t, 2H, J=6.4 Hz), δ=6.373-6.395 (d, 1H, J=8.4 Hz), δ=7.546-7.563 (m, 2H), δ=9.664 (s, 1H).

Example 60

The Preparation of the Compound of Formula 3

The compound of formula 2 (23.0 g, 0.084 mol), Phosphorus ylide (0.8 g, 0.133 mol) and 400 ml N,N-dimethylformamide were charged into a two-neck flask and stirred at reflux for 5 to 10 hours. The reaction was monitored by TLC until the completion of the reaction. Purification by column chromatography afforded 28 g the compound of formula 3 as yellow viscous liquid, with a yield of 90%.

$^1$HNMR (400 MHz, CDCl$_3$): δ=1.315-1.351 (t, 3H, J=7.2 Hz), δ=1.909-1.976 (m, 2H), δ=2.074 (s, 3H), δ=2.144-2.147 (d, 3H, J=1.2 Hz), δ=2.984-3.026 (t, 2H, J=8.4 Hz), δ=3.192-3.227 (t, 2H, J=7.2 Hz), δ=3.424-3.466 (t, 2H, J=8.4 Hz), δ=4.157-4.189 (t, 2H, J=6.4 Hz), δ=4.215-4.269 (m, 2H), δ=6.414-6.434 (d, 1H, J=8.4 Hz), δ=7.190-7.211 (m, 2H), δ=7.600 (s, 1H).

The compounds in examples 61 to 71 were prepared according the procedure described in example 60, wherein W is selected from various hydroxyl-protecting groups, X is hydrogen, and R7 is selected from various carboxyl-protecting groups. The results were summarized in following table:

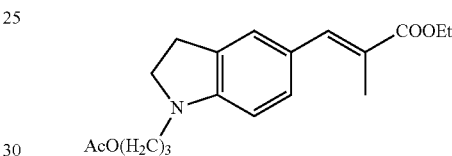

| Example | Product | W | R⁷ | Yield (%) | m/z |
|---|---|---|---|---|---|
| 61 | A-2-a | trifluoroacetyl | methyl | 93.2% | 371/372 |
| 62 | A-2-b | allyloxy-carbonyl | methyl | 89.1% | 359/360 |

-continued

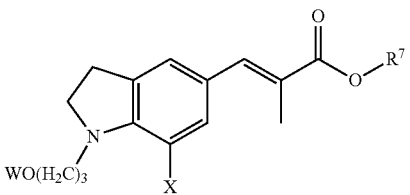

A-2

| Example | Product | W | $R^7$ | Yield (%) | m/z |
|---|---|---|---|---|---|
| 63 | A-2-c | tert-butyl-carbonyl | trifluoro-methyl | 91.0% | 429/430 |
| 64 | A-2-d | trimethylsilyl | benzyl | 85.2% | 423/424 |
| 65 | A-2-e | tert-butyl-dimethylsilyl | p-methoxy-benzyl | 86.4% | 495/496 |
| 66 | A-2-f | benzoyl | p-nitrobenzyl | 88.7% | 500/501 |
| 67 | A-2-g | p-methoxy-benzyl | p-chloro-benzyl | 74.5% | 505/506 |
| 68 | A-2-h | p-methoxy-carbobenzoxy | benzyl | 84.1% | 515/516 |
| 69 | A-2-i | p-nitrobenzy | propyl | 81.7% | 438/439 |
| 70 | A-2-j | p-chlorobenzyl | ethyl | 83.5% | 413/415 |
| 71 | A-2-k | benzyl | ethyl | 81.3% | 379/380 |

Example 72

The Preparation of the Compound of Formula 4

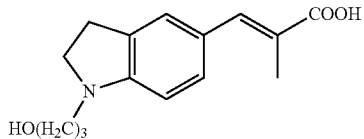

4

The compound of formula 3 (20.0 g, 0.06 mol) was charged into an one-neck flask and dissolved in 430 ml methanol. A solution of NaOH (3.6 g, 0.09 mol) in 50 mL water was added and stirred with an internal temperature of 10~25° C. The reaction was monitored by TLC until the completion of the reaction. Most of methanol was removed by distillation under reduced pressure. The mixture was extracted with ethyl acetate and the aqueous layer was adjusted to pH=3-4 with diluted hydrochloric acid, and then filtrated to afford 13.7 g the compound of formula 4 as a yellow solid, with a yield of 87.7%.

$^1$HNMR (400 MHz, DMSO): δ=1.668-1.704 (m, 2H), δ=2.030-2.032 (d, 3H, J=0.92 Hz), δ=2.915-2.957 (t, 2H, J=8.4 Hz), δ=3.153-3.189 (t, 2H, J=7.2 Hz), δ=3.393-3.435 (t, 2H, J=8.4 Hz), δ=3.464-3.495 (t, 2H, J=6.4 Hz), δ=4.453 (s, 1H), δ=6.474-6.495 (d, 1H, J=8.4 Hz), δ=7.156-7.201 (m, 2H), δ=7.470 (s, 1H), δ=12.133 (s, 1H).

The example 72 was repeated by subject the products obtained in example 61 to 66 as starting materials to hydrolyzation, to obtain the compounds in examples 73 to 78, and the results were summarized in the following table:

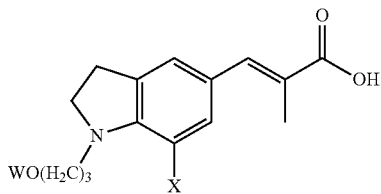

A-3

| Example | Product | Starting marital | Reagent | Yield (%) |
|---|---|---|---|---|
| 73 | A-3-2 | A-2-a | NaOH | 88.3 |
| 74 | A-3-3 | A-2-b | NaOH | 86.8 |
| 75 | A-3-4 | A-2-c | KOH | 86.7 |
| 76 | A-3-5 | A-2-d | NaHCO$_3$ | 76.3 |
| 77 | A-3-6 | A-2-e | Na$_2$CO$_3$ | 82.1 |
| 78 | A-3-7 | A-2-f | NaOH | 89.1 |

Example 79

The Preparation of the Compound of Formula 5

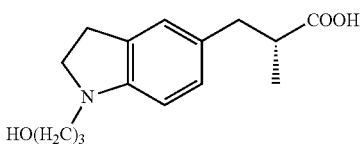

5

The compound of formula 4 (130 mg, 0.5 mmol) and catalyst Ir(L$_1$)(L$_2$)$_n$Y (9 mg, 0.002 mmol) (the catalyst with R$^3$ being phenyl, R$^4$ being benzyl, L$_2$ being Cyclooctene, n being 1 and Y being tetrafluoro borate radical) (the catalyst was supplied by Zhejiang Jiuzhou Pharmaceutical Co., Ltd) were weighted in the reaction inner tube with a stirring bar. Triethylamine (50 mg, 0.5 mmol) and 2 ml anhydrous methanol were added. After increasing the hydrogen pressure up to 0.6 Mpa, the reaction mixture was stirred at 60° C. for 1 hour. Then the stirring was stopped, the hydrogen was released. After the system was concentrated, it was diluted with 10 ml ether and was adjusted with 3N hydrochloric acid water solution to acidity. The layers were separated, and the aqueous layer was extracted with ether for two times. The combined organic layers were washed with saturated brine and dried over anhydrous sodium sulfate to afford 120 mg the compound of formula 5. The conversion rate is over 99% analyzed through $^1$HNMR, the ee value is over 99% analyzed through chiral HPLC analysis. The residue was purified by column chromatography to afford the product, with a yield of 95.0%.

$^1$HNMR (400 MHz, DMSO): δ=1.002-1.018 (d, 3H, J=6.4 Hz), δ=1.655-1.691 (m, 2H), δ=2.413-2.534 (m, 2H), δ=2.736-2.839 (m, 3H), δ=3.017-3.056 (t, 2H, J=7.2 Hz), δ=3.217-3.258 (t, 2H, J=8.4 Hz), δ=3.473-3.504 (t, 2H, J=6.4 Hz), δ=4.453 (s, 1H), δ=6.365-6.384 (d, 1H, J=8.4 Hz), δ=6.775-6.795 (d, 1H, J=8 Hz), δ=6.843 (s, 1H), δ=12.034 (s, 1H).

MS: SIL50: 263.1521.

The compounds in example 80 to 88 was prepared according to the procedure described in example 79, wherein the catalyst Ir(L$_1$)(L$_2$)$_n$Y was selected from various substituent groups and the results were summarized in the following table:

| Example | R³ | R⁴ | L₂ | n | Y | ee (%) | Yield (%) |
|---|---|---|---|---|---|---|---|
| 80 | phenyl | hydrogen | Cyclooctene | 1 | chloride ion | >99 | 88 |
| 81 | phenyl | ethyl | Cyclooctene | 1 | trifluoroacetate ion | | 90 |
| 82 | 2,5-diisopropyl phenyl | benzyl | 1,5-cyclo-octadiene | 1 | tetra(3,5-bis (trifluoromethyl) phenyl)borate radical | >99 | 93 |
| 83 | 2,5-diisopropyl phenyl | phenyl | 1,5-cyclo-octadiene | 1 | tetraphenyl borate radical | >99 | 93 |
| 84 | p-methyl phenyl | ethyl | ethylene | 1 | hexafluoro phosphate ion | >99 | 94 |
| 85 | 2-isobutyl phenyl | benzyl | 1,5-hexadiene | 2 | trifluoro methanesulfonate ion | >99 | 92 |
| 86 | p-methyl phenyl | p-methyl phenyl | 1,5-hexadiene | 2 | perchlorate ion | >99 | 94 |
| 87 | 3,5-diisopentyl phenyl | 3,5-diisopentyl phenyl | norbornadiene | 2 | nitrate radical | >99 | 93 |
| 88 | 3-isopropyl phenyl | 4-methyl benzyl | norbornadiene | 2 | bisulphate radical | >99 | 91 |

Example 89

The Preparation of the Compound of Formula 6-1 (W in the Compound of Formula 6 is Acetyl)

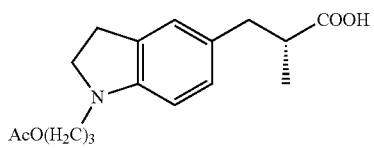

6-1

To a solution of the compound of formula 5 (2.6 g, 0.01 mol) in 40 ml THF was added triethylamine (1.52 g, 0.015 mol) and stirred. Acetyl chloride (1.2 g, 0.015 mol) was added drop wise at 0~5° C. After completion of the addition, the resulting mixture was reacted in normal temperature for 12 hours. After completion of the reaction, solvent removed by distilled under reduced pressure. The residue was extracted with ethyl acetate, washed with water for 2~3 times, dried over anhydrous sodium sulfate and concentrated to afford 2.82 g the compound of formula 6-1 as light yellow viscous liquid, with a yield of 92.3%.

¹HNMR (400 MHz, CDCl₃): δ=1.143-1.160 (d, 3H, J=10.8 Hz), δ=1.911-1.946 (m, 2H), δ=2.070 (s, 3H), δ=2.512-2.566 (m, H), δ=2.668-2.686 (m, H), δ=2.906-2.946 (t, 2H, J=8.4 Hz), δ=2.964-2.995 (m, H), δ=3.095-3.131 (t, 2H, J=7.2 Hz), δ=3.293-3.334 (t, 2H, J=8.4 Hz), δ=4.166-4.182 (t, 2H, J=3.2 Hz), δ=6.378-6.398 (d, 1H, J=8 Hz), δ=6.861-6.881 (d, 1H, J=8 Hz), δ=6.903 (s, 1H).

Example 90

The Preparation of the Compound of Formula 6-2 (W in Compound 6 is Benzyl)

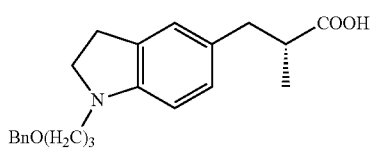

6-2

The procedure of example 72 was repeated using benzoyl bromide (2.57 g, 0.015 mol) as starting material to obtain the compound of formula (6-2) 2.74 g, with a yield of 77.6%.

All the documents mentioned in the present invention are incorporated herein by reference, as if each of them is individually incorporated. Further, it would be appreciated that the foregoing description presents specific embodiments and generic principles of the invention. Having read the above described teaching of the invention, one skilled in the art could make various changes or modifications to the invention without departing from the spirit and scope of the invention. These equivalents would still be within the scope of the invention.

The invention claimed is:

1. A compound of formula (A):

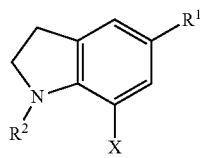

A wherein: X is bromine, R¹ is formoxyl or a group selected from the following structures:

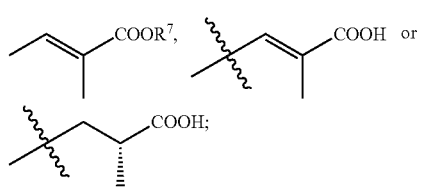

R⁷ is a protecting group of carboxyl;
R² is 3-hydroxypropyl or a group having the following structure:

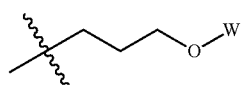

wherein W is a protecting group of hydroxyl.

2. The compound according to claim 1, characterized in that, the W is selected from acetyl, trifluoroacetyl, allyloxycarbonyl, tert-butylcarbonyl, trimethylsilyl, tert-butyldimethylsilyl, benzoyl, triphenylmethyl, p-methoxybenzyl, p-methoxybenzoxycarbonyl, p-nitrobenzyl, m-nitrobenzyl, p-chlorobenzyl, m-chlorobenzyl, p-bromobenzyl, m-bromobenzyl, benzyl.

3. The compound according to claim 1, characterized in that, $R^7$ is selected from alkyl or substituted alkyl.

4. The compound according to claim 3, characterized in that, the alkyl is selected from methyl, ethyl and propyl; the substituted alkyl is selected from trichloromethyl, trifluoromethyl, benzyl, p-methoxybenzyl, p-nitrobenzyl, m-nitrobenzyl, p-chlorobenzyl, m-chlorobenzyl, p-bromobenzyl, m-bromobenzyl or benzyl.

5. The compound according to claim 1, characterized in that, the compound is selected from the compounds having the following structures:

A-1

A-2

A-3

A-4 wherein W, X, $R^7$ are as defined in claim 1.

6. A method for the preparation of compound of formula (A-2) according to claim 5, comprising reacting the compound of formula (A-1) with the compound of formula C,

A-2

A-1

C $Ph_3P=C(CH_3)COOR^7$, wherein X is hydrogen or bromine, W is a protecting group of hydroxyl, $R^7$ is a protecting group of carboxyl.

7. The method according to claim 6, comprising reacting the compound of formula (A-2) in the presence of base by hydrolyzation to afford the compound of formula (A-3),

A-3

A-2 wherein, X is hydrogen or bromine, W is a protecting group of hydroxyl, $R^7$ is a protecting group of carboxyl.

8. The method according to claim 7, wherein, the base is alkali metal base.

9. The method according to claim 7, comprising reacting the compound of formula (A-3) in the presence of base by asymmetric catalytic hydrogenation to afford the compound of formula (A-4),

A-4

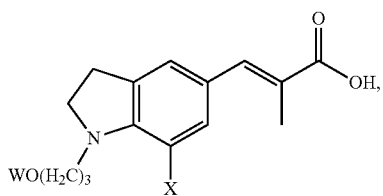

wherein, X is hydrogen or bromine.

10. The method according to claim 9, wherein, the catalyst is Ir(L$_1$)(L$_2$)nY, in which L$_1$ is defined as (Sa,S)-SIPHOX;

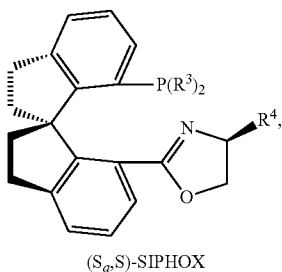

wherein R$^3$ is aryl; R$^4$ is hydrogen, alkyl, aryl or aralkyl; L$_2$ is cyclooctene, 1,5-cyclooctadiene, ethylene, 1,5-hexadiene or norbornadiene; n is 1 or 2; Y is chloride ion, bromide ion, iodide ion, fluoride ion, trifluoroacetate ion, tetrafluoro borate radical, tetra(3,5-bis(trifluoromethyl)phenyl)borate radical, tetraphenyl borate radical, hexafluoro antimonite radical, hexafluoro phosphate ion, trifluoro methanesulfonate ion, methanesulfonate ion, perchlorate ion, perbromate ion, periodate ion, nitrate radical, bisulphate radical or acetylacetonate ion.

11. The method according to claim 9, wherein, the base is alkali metal base or amines.

12. The method according to claim 9, wherein, further comprising the step of, in the presence of diphenylphosphoryl azide and diisopropylethylamine, reacting the compound of formula (A-4) with the compound of formula (E) to obtain the compound of formula (D),

R$^6$OH,       E

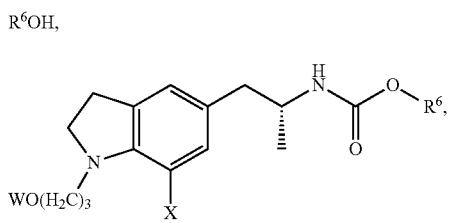

wherein, X, W is as defined in claim 1, R$^6$ is a protecting group of carboxyl.

13. The method according to claim 12, wherein, the R$^6$ is tert-butyl, ethenyl, allyl, benzyl, p-methoxybenzyl, p-nitrobenzyl or diphenylmethyl.

14. A method for the preparation of the compound of formula (A) according to claim 1, wherein, comprising reacting the compound of formula (B) with bromine,

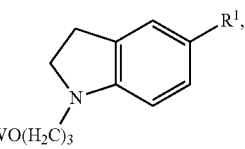

Wherein, X is hydrogen or bromine, W and R$^7$ areas defined in claim 1.

15. The method according to claim 11, characterized in that, the alkali metal base is lithium hydroxide, sodium hydroxide, potassium hydroxide, cesium hydroxide, sodium bicarbonate, potassium bicarbonate, sodium carbonate, potassium carbonate or cesium carbonate; the amines is arylamine or alkylamine.

16. The method according to claim 11, characterized in that, the amines is aniline, N,N-dimethylaniline, N-methyl morpholine, diisopropylamine, N,N-isopropylethylamine, triethylamine or pyridine.

17. The method according to claim 8, characterized in that, the alkali metal base is lithium hydroxide, sodium hydroxide, potassium hydroxide, cesium hydroxide, sodium carbonate, potassium carbonate, sodium bicarbonate or potassium bicarbonate.

18. The compound according to claim 1, characterized in that, the compound is selected from the compounds having the following structures:

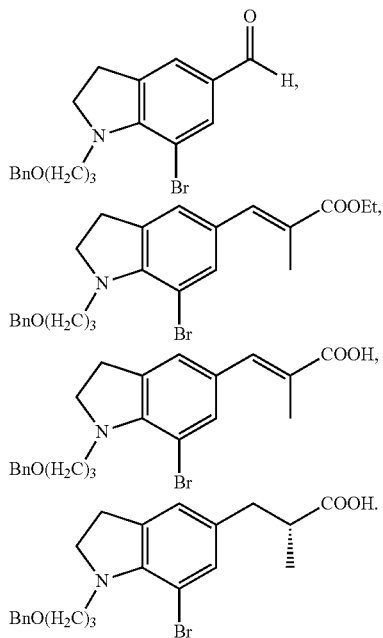

* * * * *